(12) United States Patent
Publicover et al.

(10) Patent No.: US 9,931,069 B2
(45) Date of Patent: *Apr. 3, 2018

(54) SYSTEMS AND METHODS FOR MEASURING REACTIONS OF HEAD, EYES, EYELIDS AND PUPILS

(71) Applicant: Google Inc., Mountain View, CA (US)

(72) Inventors: Nelson G. Publicover, Reno, NV (US); William C. Torch, Reno, NV (US)

(73) Assignee: Google LLC, Mountain View, CA (US)

( * ) Notice: Subject to any disclaimer, the term of this patent is extended or adjusted under 35 U.S.C. 154(b) by 105 days.

This patent is subject to a terminal disclaimer.

(21) Appl. No.: 14/569,303

(22) Filed: Dec. 12, 2014

(65) Prior Publication Data
US 2016/0166190 A1 Jun. 16, 2016

Related U.S. Application Data

(63) Continuation of application No. 13/113,006, filed on May 20, 2011, now Pat. No. 8,911,087.

(51) Int. Cl.
*A61B 3/00* (2006.01)
*A61B 3/14* (2006.01)
(Continued)

(52) U.S. Cl.
CPC ............ *A61B 5/162* (2013.01); *A61B 3/0008* (2013.01); *A61B 3/0025* (2013.01); *A61B 3/112* (2013.01);
(Continued)

(58) Field of Classification Search
USPC ....... 351/200, 203, 205, 206, 209, 210, 211, 351/221, 222, 223, 245, 243, 246
See application file for complete search history.

(56) References Cited

U.S. PATENT DOCUMENTS

| 4,825,788 A | 5/1989 | Julien |
| 5,360,985 A | 11/1994 | Hiyoshi et al. |

(Continued)

FOREIGN PATENT DOCUMENTS

| JP | 2008000205 | 1/2008 |
| JP | 2010063621 | 3/2010 |

(Continued)

OTHER PUBLICATIONS

European Examination Report dated Jan. 16, 2017 for EP Application No. 12789063.0-1666, 4 pages.

*Primary Examiner* — Brandi Thomas

(57) ABSTRACT

Systems and methods are provided to measure reaction times and/or responses for head, eye, eyelid movements, and/or changes in pupil geometry. The system includes eyewear or headwear including one or more eye-tracking cameras for monitoring the position and geometry of at least one eye and its components of the user, one or more scene cameras for monitoring the user's surroundings, and one or more processors to determine reaction times. Optionally, the system may include one or more of a multi-axis accelerometer to monitor head movements, light sources to trigger visual evoked responses, and/or electronic inputs that may be used to indicate the time of occurrence of external reference events. Measured reaction times and other measurements may be monitored for use in a range of applications. Responses and reaction times may be measured continuously over extended periods, even over a lifetime to measure consequences of the aging process.

18 Claims, 7 Drawing Sheets

(51) Int. Cl.
  *A61B 5/16*   (2006.01)
  *A61B 3/113*  (2006.01)
  *A61B 3/11*   (2006.01)
  *A61B 5/11*   (2006.01)
  *A61B 5/00*   (2006.01)

(52) U.S. Cl.
  CPC ............... *A61B 3/113* (2013.01); *A61B 3/14* (2013.01); *A61B 5/1103* (2013.01); *A61B 5/1114* (2013.01); *A61B 5/6803* (2013.01); *A61B 2560/0242* (2013.01); *A61B 2562/0204* (2013.01)

(56) References Cited

U.S. PATENT DOCUMENTS

| | | |
|---|---|---|
| 5,555,895 A | 9/1996 | Ulmer et al. |
| 5,748,113 A | 5/1998 | Torch |
| 6,116,736 A | 9/2000 | Stark et al. |
| 6,260,968 B1 | 7/2001 | Stark et al. |
| 6,820,979 B1 | 11/2004 | Stark et al. |
| 7,147,327 B2 | 12/2006 | Okamoto et al. |
| 7,346,195 B2 | 3/2008 | Lauper et al. |
| 7,488,294 B2 | 3/2009 | Torch |
| 7,515,054 B2 | 4/2009 | Torch |
| 7,630,524 B2 | 12/2009 | Lauper et al. |
| 7,670,002 B2 | 3/2010 | Stark et al. |
| 8,235,526 B2 | 8/2012 | Stark et al. |
| 8,323,216 B2 | 12/2012 | Fabian |
| 8,911,087 B2 * | 12/2014 | Publicover ............. A61B 3/113 351/200 |
| 9,402,542 B2 | 8/2016 | Stark et al. |
| 2004/0006287 A1 | 1/2004 | Epley |
| 2004/0239878 A1 | 12/2004 | Bradley |
| 2007/0066916 A1 | 3/2007 | Lemos |
| 2007/0273611 A1 * | 11/2007 | Torch ................... A61B 3/0066 345/8 |
| 2008/0309616 A1 | 12/2008 | Massengill |
| 2011/0077548 A1 | 3/2011 | Torch |
| 2015/0154474 A1 | 6/2015 | Nada et al. |

FOREIGN PATENT DOCUMENTS

| | | |
|---|---|---|
| WO | 2005046464 | 5/2005 |
| WO | 2007125794 | 11/2007 |

* cited by examiner

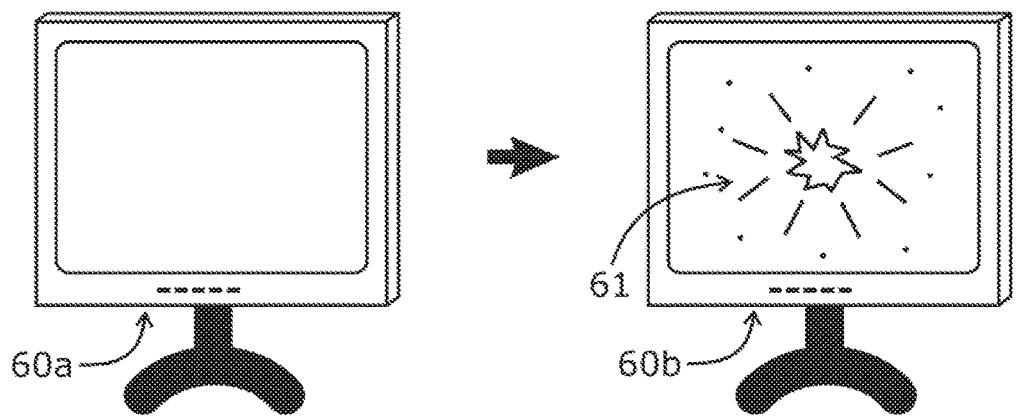
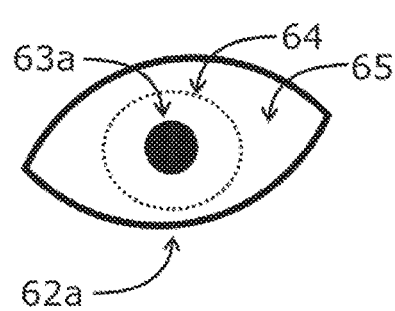
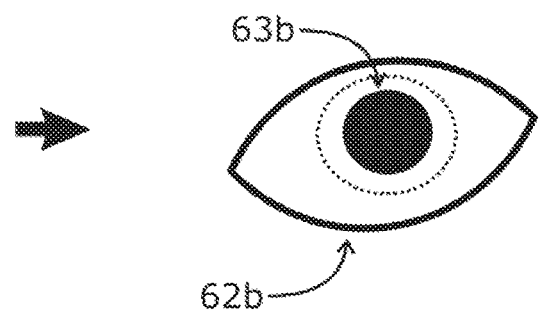
FIG. 6A    FIG. 6B
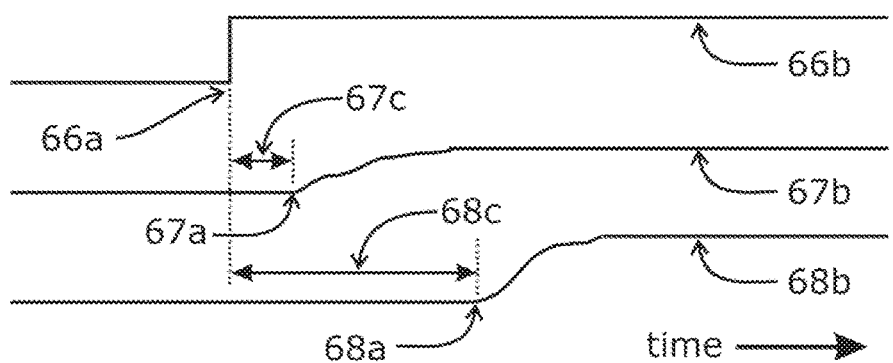
FIG. 6C

SYSTEMS AND METHODS FOR MEASURING REACTIONS OF HEAD, EYES, EYELIDS AND PUPILS

RELATED APPLICATION DATA

The present application is a continuation of application Ser. No. 13/113,006, filed May 20, 2011, issuing as U.S. Pat. No. 8,911,087, the entire disclosure of which is expressly incorporated by reference herein.

STATEMENT REGARDING FEDERALLY SPONSORED RESEARCH AND DEVELOPMENT

The U.S. Government may have a paid-up license in this invention and the right in limited circumstances to require the patent owner to license others on reasonable terms as provided for by the terms of Department of Defense (US Army) Contract No. W81XWH-05-C-0045, U.S. Department of Defense Congressional Research Initiatives No. W81XWH-06-2-0037 and W81XWH-09-2-0141, and U.S. Department of Transportation Congressional Research Initiative Agreement Award No. DTNH 22-05-H-01424.

FIELD OF THE INVENTION

The present invention relates to apparatus and methods for unobtrusively measuring reaction times and/or other responses following events that take place in the general environment of a device wearer and consequential changes in the head, eye, eyelid, and/or pupil of the device wearer.

BACKGROUND

The response of an individual to a spontaneous or intentionally generated event involves a number of complex neurological and physiological steps including detection, conductive neural pathways, synaptic connections, perception, cognition, and neuro-muscular control. Normal activities or disorders in any of the anatomical structures or chemistries involved in these steps, as well as physiological awareness and training, can affect an individual's response magnitudes and reaction times. An unobtrusive device that measures reaction times and/or other responses of an individual over brief (i.e., seconds to minutes) or prolonged (i.e., days or even years) time periods has a number of medical, sports training, human factors, safety, diagnostic, military, law enforcement, gaming, and other applications.

Applications that involve sensing and machine vision are becoming increasingly common-place. In part, this has arisen as a result of technological advances in the electronics and software development industries, and decreases in the cost of sensors, cameras, and information processing units. For example, recent advances in accelerometers based on microelectromechanical systems (MEMS) techniques have made them inexpensive, miniature, sensitive, robust, low-power, multi-axial (within a single package), and easy to use. Accelerometers can be used to sense gravitational orientation as well as multi-dimensional movements.

Similarly, cameras that employ complementary metal-oxide semiconductor (CMOS) or charge-coupled device (CCD) approaches, can be inexpensive, miniature, optically sensitive, low-power, robust, and high resolution. Using such cameras and image processing units, automated object identification and tracking are increasingly being used in a number of diagnostic, human performance, commercial, and control applications.

With the exception of events that cause head trauma, most movements of the head are relatively slow (e.g., less than about ten Hertz (10 Hz)). Thus, sample rates to accurately monitor head movement may be in the range of tens of samples/second. Similarly, most measurements of eye, eyelid, and pupillary responses and reaction times, which may have reaction times in the range of tenths of a second to seconds, require the frame rates commonly available in modern, household cameras and video displays (i.e., 30-120 frames per second). Research laboratories and some other applications may demand measurements from accelerometers and cameras that are capable of higher sample rates but at an increased cost; however, eyewear and headwear devices can take advantage of commonly-available miniature, low-power cameras and sensing components.

Many head- and eye-tracking systems use cameras and illuminators that are located at a considerable distance (e.g., greater than about ten centimeters (10 cm)) from the wearer's head. As the distance away from the wearer's head is increased, a head/eye tracking apparatus generally becomes less obtrusive; however, it becomes increasingly difficult to accurately measure the location of a wearer's head and/or eyes because of the need for higher spatial resolution by cameras. Also, wide-ranging head movement may cause complete loss of the ability to track the location of a wearer's eye and its components.

With the advent of modern-day microelectronics and micro-optics, it is possible to unobtrusively mount the components for measuring reaction times or other responses on eyewear (e.g., eyeglasses frames) or headwear (e.g., helmet, mask, goggles, virtual reality display) including those devices disclosed in U.S. Pat. Nos. 6,163,281, 6,542,081, 7,488,294, or 7,515,054, the entire disclosures of which are expressly incorporated by reference herein. The use of low-power and miniature cameras, sensors, and electronics permits a head-mounted system to be non-tethered through the use (optionally) of a battery power source. Furthermore, recent advances in wireless telecommunications allow reaction time results to be transmitted in real-time to other computing, data storage, or control devices. As a result of these technological advances in a number of fields, an eyewear- or headwear-based response and reaction time monitoring system may be unobtrusive, light-weight, low-power, portable, and convenient to use.

Non-invasive tools for physiological monitoring and medical diagnostics are increasingly commonplace in clinics, hospitals, research laboratories, and even homes and public areas, such as grocery stores and pharmacies. If such tools are constructed to be unobtrusive, simple to use, and portable; they gain even further potential in their acceptance by the general public and subsequent applications to monitor longer-term response trends (versus one-time or "snap-shot" measurements). This is in addition to their capability to react in real-time if certain conditions are encountered; for example, if a state of drowsiness is determined while driving a vehicle.

Monitoring responses of the head and eyes is particularly useful in assessing both central and peripheral nervous system physiological function and disorders. For example, reaction times and/or other responses of the pupil are influenced by a chain of anatomical structures including photosensitive ganglion cells and the retinohypothalamic tract within the optic nerve, the pretectal nucleus within the upper midbrain, and the Edinger-Westphal nucleus with axons running along left and right oculomotor nerves that synaptically connect to ciliary ganglion nerves that, in turn, innervate constrictor muscles of the iris. Disorders or conditions (e.g., the presence of barbiturates) that affect any of the structures within this chain may produce consequential changes in reaction times and/or other responses that may be monitored non-invasively and unobtrusively. Initial constriction of the pupils by alcohol or opioids; or dilation by a wide range of drugs including lysergic acid diethylamide (LSD), cocaine, amphetamines, 3,4-methylenedioxymethamphetamine (MDMA, also known as ecstasy), mescaline, and so on; may also affect measured responses and reaction times.

Reaction times and/or other responses may be used to probe even deeper into cognitive functions of the brain. An unobtrusive tool for substantially continuously monitoring reaction times and/or other responses of the head and eyes may lend valuable quantitative measurements to perceptions that we are all familiar with, including sensing fear, alarm, or whether someone is telling the truth. This may result in a number of applications including substantially continuous monitoring of the elderly for diagnostic purposes as well as an input in determining emergency situations. An example of an application where a clinician may take advantage of the quantitative nature of such measurements is in the assessment of many anxiety disorders such as post-traumatic stress disorder (PTSD). Measuring avoidance behaviors and difficulty concentrating along with exaggerated responses to events that startle may be monitored and used for assessment and tracking of such disorders.

Measurements of evoked pupillary responses have been used in a wide range of assessments of "cogitative load" or "mental effort" and associated disorders. Under normal physiological conditions, the presentation of multiple stimuli in timed sequences can increase pupillary dilation responses. An increase in this effect may be indicative of various forms of dementia.

Conversely, a goal of sports training is to improve performance by decreasing reaction times. Anticipation and experience may each reduce reaction times by (as generally believed) reducing any decision times and strengthening synaptic connections. An unobtrusive device that may measure reaction times and/or other responses over prolonged periods may be valuable in monitoring, for example, the effectiveness of training regimes.

SUMMARY

The present invention is directed to systems, apparatus, and methods for determining reaction times and/or other responses of the device wearer. In an exemplary embodiment, the apparatus, systems, and methods herein may provide a method and system that measures reaction times and/or other responses, e.g., magnitude of responses, of the head, eye, eyelid, and/or pupil for various applications.

For example, the apparatus, systems, and methods herein relate to the use of machine vision and other techniques to identify 1) the time of occurrence of events that happen in the environment of a device wearer, and/or 2) consequential movements of the head and/or small movements of at least one eye of the device wearer including eyelid and eyeball displacements, and/or changes in the geometry of a pupil, e.g., to measure, analyze, and/or determine responses of the wearer. The difference between the time of occurrence of environmental events and the time of the device wearer's response is commonly referred to as a "reaction time" or "response time." The term "reaction time" is frequently used to describe consequential responses to events that occur spontaneously. In the case when an eye movement or pupillary response is intentionally evoked using a light source or some other means, the term "response time" is more common in the scientific and medical literature.

Generally, the term "reaction time" will be used herein to refer to the difference between the time of an event and the time that a reaction to that event is detected that exceeds a predetermined threshold, e.g., resulting in a length of time associated with a binary change in reaction. It is to be understood that the use of the term "reaction time" is intended to include "response time," "response delay," "reflex time," and other equivalent terms.

Similarly, the "magnitude" of a response may also be measured and/or analyzed in addition to or instead of the "reaction time" of the response. Examples of magnitudes of responses include measurements such as the total spatial displacement of anatomical structures of a device user (e.g., an eye or eyelid), a rotational movement such as that generated by turning the head, the amplitude of a change in velocity or acceleration of anatomical structures, changes in area or volume such as those experienced during pupillary dilation or constriction, and the like.

Similarly, in the description below, references to sensing movements of a device wearer's head also may include any structure or component of the head that may simultaneously move and be sensed by eyewear or headwear when worn by the device wearer. This includes, for example, the skull, brain, hair, ears, forehead, eye sockets, nose, cheeks, chin, jaw, and the like. Along the same lines, references to responses and movements of the device wearer's eye incorporate all sub-components of the eyes including the eyeball, iris, cornea, lens, sclera, ciliary body, vitreous body, and the like. References to responses and changes of the device wearer's pupil include structures and components that can be imaged within pupillary images such as the lens, retina, fovea, optic disk, sphincter pupillae, dilator pupillae, and the like. Similarly, references to movements and changes in the device wearer's eyelid include monitoring the eyelashes, eyebrow, folds within the eyelid, and the like.

A low-cost, unobtrusive, portable platform that may repeatedly measure responses and reaction times has a wide range of applications. A small number of examples include monitoring the degree of fatigue of an individual, assessing driver or pilot awareness, assessing the effects of drugs or alcohol, diagnosing post-traumatic stress disorder, tracking human performance with age, determining the effectiveness of training or exercise, controlling various aspects of games, acquiring foundational clinical data to assess neurological or cognitive disorders, diagnosing and monitoring degenerative eye conditions, and monitoring the awareness of individuals or animals who are otherwise not able to communicate. Sectors and industries that may make use of reaction time measurements include medicine, military, law enforcement, security, human performance, sports medicine, rehabilitation engineering, police, research laboratories, and toys.

In one embodiment, a system for determining reaction times and/or other responses includes a device configured to be worn on a person's head, an input to determine reference times, an eye-tracking camera mounted on the device and positioned for viewing a first eye of the wearer of the device, a processor that determines the locations of anatomical structures within eye-tracking camera images, and a processor that uses the reference times and eye-tracking locations to determine reaction times and/or other responses of the wearer's eye, eyelid, and/or pupil.

In some embodiments, reaction times of the device wearer may be calculated by determining the times of occurrence of reference events and consequential responses by the device wearer. The apparatus and systems herein may accept electronic signals to provide temporal reference markers or use one or more scene cameras mounted on eyewear or headwear to optically identify the times of occurrence of changes within the environment. In an exemplary embodiment, the device may include an accelerometer to measure multi-axis movements of the head, and one or more unobtrusive eye-tracking cameras may be mounted on the eyewear or headwear to track movements of, or changes in, one or more eyes of the device wearer. Reaction times and/or other response measurements of the device wearer may be used in a wide range of fields including medical, legal, security, sports, computer gaming, and human factors.

For example, systems and methods herein may use eye-tracking cameras mounted on eyewear or headwear to track the locations of one or both eyes similar to the embodiments described in the references incorporated by reference elsewhere herein. Eye-tracking cameras and one or more associated processing units may be used to identify and track reference locations within eye-tracking camera images. Reference locations may include, for example, the center of a pupil, edges of a pupil, center of the iris, edges of the iris, and locations of the whites of the eye or sclera. For reaction time measurements, particular attention is paid to the times when significant movements of reference locations are initiated.

Systems and methods herein may additionally use eye-tracking cameras mounted on eyewear or headwear to track the locations of one or both eyelids. Eye-tracking cameras and one or more associated processing units may utilize the obscuring of structures of the eyeball (e.g., pupil, iris, sclera) and/or changes in color, brightness and/or texture in the region of the eye that result from eyelid closure. In general, absent neuro-muscular disorders, the eyelid sweeps the field-of-view as horizontal waves of disruption within eye-monitoring camera images. For reaction or response time measurements, particular attention is paid to the times when the eyelid initially closes, covering the eye including the pupil, and/or as the eyelid re-opens.

Systems and methods herein may additionally use eye-tracking cameras mounted on eyewear or headwear to track the size of one or both pupils. Eye-tracking cameras and one or more associated processing units may detect the edges of the pupils as regions where there is high spatial contrast in luminance or texture compared to the iris. Geometric shapes, such as circles or ellipses, may be superimposed on images to determine a size that best overlaps with the edges of the pupil. Areas may then be calculated based on well-known formulae for the geometric shapes.

Additionally or alternatively, the area occupied by a pupil may be calculated by determining the number of pixels that meet certain image recognition criteria, such as exceeding a certain darkness level in an area where there are a significant number of other dark pixels. This takes advantage of the fact that, under most lighting conditions, pupils appear dark and within a certain size range. Areas may then be calculated, for example, based on counts of the number of adjoining dark pixels within a relatively large region of dark pixels.

Additionally or alternatively, with careful control of lighting, either transcutaneously from the side of the head or aimed directly (within about ±three degrees (3°) of the perpendicular to the surface of the cornea) into the pupil, it is possible to generate a so-called "white-eye," "red-eye," or "while-pupil" effect. Under these conditions, it is possible to calculate areas based on the number of bright pixels and/or by detecting the edges of bright pupil regions.

For reaction or response time measurements, attention may be paid to the times when the pupil begins to constrict or dilate. Compared to response times of the eye and eyelid, pupillary responses are generally more delayed, i.e., with longer reaction or response times.

In order to measure a reaction time, the time of occurrence of an event (i.e., reference time) that is causal to the reaction must be determined. There are many potential sources for events that may produce responses by the head, eye, eyelid, and/or pupil. These may include images, sounds, flashes of light, movement, blunt force, and the like. The eyewear or headwear platform is designed to accept different inputs for reference time measurements from these different modalities.

In accordance with an exemplary embodiment, systems and methods are provided that use one or more scene cameras to optically monitor the environment surrounding the device wearer. Scene cameras and one or more associated processing units are used to identify and track reference objects within scene camera images. Object recognition based on machine vision techniques, which are well-known in the art, may use identifiable characteristics within images of an object such as an object's brightness, size, shape, color, and the like; or combinations of these characteristics. The presence or absence of an object within a scene, such as the abrupt display of an image on a computer monitor or the revealing of a photograph, may, for example, be used as a temporal reference.

In accordance with another embodiment, systems and methods are provided that use the location of one or more objects in scene camera images to determine reference times. For example, reference times may be triggered when an object enters a certain location or region within scene camera images. A sports-related example is the registration of a reference time when a projectile, such as a baseball, reaches a selected location (e.g., near a batter) within a scene camera image. Similarly, reference times may be registered when an object attains a certain velocity or acceleration within scene camera images. Additionally, reference times may be triggered when there is a change in an object's characteristics such as brightness level, color, size, shape, and the like in scene camera images.

In addition or alternatively, one or more scene cameras that survey the environment around a device wearer may be used to determine reference times by tracking specific objects within scene camera images, and to determine the occurrence of consequential head movements. In the example where there is movement of one or more scene cameras due to movement of head of the device wearer, most of the area within the scene camera images appears progressively displaced (i.e., the entire scene shifts). At a constant video frame rate, higher velocity movements of the head result in greater displacements of the background in scene camera images (except when head movements are directly toward or away from a nearby background, such as a wall). This is in contrast to the movement of smaller, specific objects within scene camera image that may be used to make reference time determinations.

In accordance with still another embodiment, an accelerometer may be included within a set of eyewear or headwear to monitor head movement. Movements of the head in response to trigger events may be used to measure head reaction times and/or other responses. A multi-axis accelerometer, e.g., that uses MEMS or other techniques to detect accelerations in up to three (3) orthogonal directions, may be used to detect accelerations of the head as well as overall head orientation relative to the gravitational field of the earth. Such accelerations may be integrated with respect to time to obtain relative head velocities in each dimension as well as head displacements (i.e., following a second integration with respect to time). For many applications, it is convenient to calculate rotational movements of the head (i.e., affixed to the eyewear or headwear containing the accelerometer) about the neck.

In accordance with another embodiment, a general purpose input connector may be included within the eyewear or headwear to allow a wide range of sensor signals to be used as a source for reference times. For example, a microphone may be connected and used to generate reference times from auditory inputs. This allows the device to measure reaction times and/or other responses to the occurrence of sounds. A simple method to register audio reference times is to monitor the onset of a sharp sound. Examples of sources of such sounds include the clapping of hands, an explosion, a starter's gun, a drum beat, a metronome, a click, and the like. More sophisticated sound-recognition techniques and algorithms are known in the art including those that recognize the occurrence of specific words, tones, or audio sequences.

In other embodiments, analog signals (i.e., signals represented as continuously varying changes in amplitude of either current or voltage) may be used as a source for reference times. For example, these may include sensing the position of an object (e.g., door, lever), intensity of ambient light, temperature, and the like. Temporal references may be registered when the amplitude of the analog signal exceeds a selected threshold or by other waveform recognition techniques.

In other embodiments, digital signals may be used as a source for reference times. In general, the time of occurrence of low-to-high and/or high-to-low transitions, i.e., binary transitions, in such signals represent time registrations. Digital signals may, for example, be generated by other control devices such as a computer, produced by a switch or push button, synchronized with the display of an image, coincident with a tactile or electrical stimulus, and the like.

In accordance with still other embodiments, it is possible to produce stimuli directly on the eyewear or headwear in order to evoke measurable responses. This configuration is particularly useful in measuring pupillary responses and reaction times. For example, light stimuli may be provided by one or more light-weight and low-power, light-emitting diodes (LEDs) aimed at one or both eyes. The LEDs and/or other light sources may be made to vary in wavelength and/or intensity. In addition or alternatively, one or more speakers may be provided, e.g., on the device or separate from the device, that may generate predetermined sounds and subsequent reaction times may be monitored.

Measuring the presence or absence of pupillary responses and reaction times may be particularly useful in medical diagnostic screening. Delays or disruption in pupillary responses may be indicative of a number of neuro-muscular or cogitative disorders. For example, under normal physiological conditions, the projection of sufficient light toward one eye should generate pupillary constriction in the other eye. Absence or delay of this response may, for example, result from lesions within the central nervous system or the presence of certain classes of drugs.

An accurate assessment of reaction times and/or the degree of responsiveness may also be particularly useful in law enforcement during, for example, screening tests for the effects of drugs and/or alcohol. In this application, it is possible to use visible light or light that is normally "invisible," i.e., beyond the visible spectrum) to evoke pupillary responses. Visible light, in the wavelength range from about 390 to 750 nanometers, may be used to evoke pupillary responses, where the threshold amplitude has been reported to be somewhat wavelength-dependent.

The use of invisible light in the near infrared spectrum, e.g., in the vicinity of 800 nanometers, may also be used to measure evoked pupillary dilations of the device wearer at times that the device wearer is not aware that measurements are being made. This protocol may be used to circumvent efforts by the device wearer to deceive law enforcement, for example, by attempting to conceal responses. Evoked responses may also, for example, be generated on the eyewear or headwear; or from an external source, such as traditional law-enforcement methods involving the sweeping of a flashlight across the region of the eyes, where reference times of when the flashlight is aimed at the eyes can be sensed and registered by either scene or eye-tracking cameras.

An illumination controller may be coupled to one or more light sources and may be configured for determining brightness based on the presence or absence of measurable pupillary responses. By repeatedly adjusting brightness levels, it is possible to determine threshold levels for evoked pupillary responses, i.e., the minimum change in light level that causes pupillary constriction or dilation at a given wavelength. Such measurements may be used in medical diagnosis and physiological monitoring. An unobtrusive eyewear platform may be particularly useful in cataloging the progression of some forms of degenerative eye diseases or age over prolonged periods (i.e., months or even years). The scene processing unit and eye-tracking processing unit may be one or more separate processors with a separate illumination controller, or may be a single processor and include the illumination controller.

In one embodiment, the illumination controller may be configured for amplitude modulation of at least the current and/or the voltage to the light source to provide the desired brightness levels at an eye. In addition or alternatively, the controller may be configured for pulse-width modulation of at least one of the current and the voltage to the light sources to provide the desired brightness levels.

In any of these embodiments; illumination, reaction time measurements, head tracking, eye tracking, and/or gaze tracking may be operated substantially continuously or intermittently. Processors, cameras, illumination, and/or other electronics may be deactivated when not in use, e.g., to conserve power. Illumination sources and other electronics may also be reduced in power or turned off for increased safety.

In accordance with still other embodiments, optionally, additional eye-tracking cameras may be provided on the eyewear or headwear platform, e.g., to simultaneously track responses in the region of both eyes. In healthy individuals, the reaction times of components of both eyes should be approximately the same. If the reaction times of the left and right eyes of an individual are divergent, measurements may be used to help diagnose physiological abnormalities or disease. For example, delayed responses in both eyes may be indicative of a central nervous system cognitive or systemic disorder whereas a delayed response in a single eye or eyelid may be indicative of a peripheral neuro-muscular anomaly.

In accordance with another embodiment, wireless transmission may be added to the eyewear or headwear to transmit information to and from remote sites. For example, images and measurements may be transmitted to remote computing devices for further analysis and display. Conversely, wireless signals indicating reference times and/or magnitudes of triggering events to be associated with measured responses of the head, eye, eyelid and/or pupil may be transmitted to the eyewear or headwear platform.

In accordance with yet another embodiment, a system is provided for determining reaction times, magnitudes of responses, and/or other responses that includes a device configured to be worn on a wearer's head; an eye-tracking camera mounted on the device oriented towards a first eye of the wearer for capturing eye-tracking images of the first eye; and one or more processors coupled to the eye-tracking camera for identifying anatomical structures of the first eye within the eye-tracking camera images. The one or more processors may be configured for identifying reference times of external events and analyzing the eye-tracking images after the reference times to determine responses of the first eye, eyelid, and pupil to the external events. For example, processor(s) may identify two or more parameters selected from: a) location of at least one of the pupil and iris in one or more dimensions, b) a size of the pupil, c) a shape of the pupil, and d) a location of the eyelid from the eye-tracking images, and detect changes in the two or more parameters to determine reaction times or other responses of the wearer to external events.

Optionally, the system may include one or more devices for detecting external events to provide reference times. For example, in one embodiment, a scene camera may be mounted on the device oriented away from the wearer for viewing an environment of the wearer and capturing scene camera images of the environment. The processor(s) may identify reference times from changes detected in the scene camera images. For example, the processor(s) may use object recognition algorithms to identify locations of objects within a field-of-view of the scene camera from the scene camera images, and identify reference times based on the times when predetermined objects are present at or absent from predetermined locations in the scene camera images. In addition or alternatively, the processor(s) may analyze the scene camera images for scene movements to determine movements of the wearer's head, and identify particular head movements with reference times.

In another embodiment, the system may include a detector for monitoring sounds or other activities within the wearer's environment. For example, a microphone may be mounted on the device for detecting sounds, and the processor(s) may be coupled to the microphone for monitoring the wearer's environment to identify predetermined sounds and associating reference times with the predetermined sounds.

In accordance with still another embodiment, a system is provided for determining reaction times, magnitudes of responses, and/or other responses that includes a device configured to be worn on a wearer's head; an eye-tracking camera mounted on the device oriented towards a first eye of the wearer for capturing eye-tracking images of the first eye; and a scene camera mounted on the device oriented away from the wearer for viewing an environment of the wearer and capturing scene camera images of the environment. One or more processors may be coupled to the eye-tracking camera for identifying anatomical structures of the first eye in the eye-tracking images, and/or to the scene camera for identifying predetermined events in the environment of the wearer from the scene camera images. For example, the one or more processors may identify a reference time when a predetermined event is identified from the scene camera images, and may monitor changes in one or more of the anatomical features identified in the eye-tracking images to determine a reaction time or other response of the wearer to the predetermined event.

In an exemplary embodiment, the processor(s) may monitor the scene camera images to identify an object in the environment of the wearer from the scene camera images, and may monitor the object to identify when the object is present at or absent from a predetermined location in the scene camera images. In this example, the reference time may be the time when the processor(s) identify that the object is present at or absent from the predetermined location. In another exemplary embodiment, the system may include an electronic object including a display, and the processor(s) may monitor the scene camera images to identify when a predetermined image is presented on the display. In this example, the reference time may be the initial time the predetermined image is displayed.

In accordance with yet another embodiment, a system is provided for determining reaction times or other responses that includes a device configured to be worn on a wearer's head; an eye-tracking camera mounted on the device oriented towards a first eye of the wearer for capturing eye-tracking images of the first eye; and a microphone for detecting sounds within an environment of the wearer. One or more processors may be coupled to the eye-tracking camera for identifying anatomical structures of the first eye in the eye-tracking images, and to the microphone for detecting predetermined sounds generated within the environment of the wearer. For example, the processor(s) may identify a reference time when a predetermined sound is detected and monitor changes in one or more of the anatomical features identified in the eye-tracking images to determine a reaction time or other response of the wearer to the predetermined sound.

In accordance with still another embodiment, a system is provided for determining reaction times or other responses that includes a device configured to be worn on a wearer's head; an eye-tracking camera mounted on the device oriented towards a first eye of the wearer for capturing eye-tracking images of the first eye; and an emitter for emitting a detectable signal towards the wearer; and a sensor mounted on the device for providing an orientation of the wearer's head. One or more processors may be coupled to the eye-tracking camera for identifying anatomical structures of the first eye in the eye-tracking images, and to the sensor for monitoring the orientation of the wearer's head.

The processor(s) may identify a reference time when the emitter is activated and monitor changes in the one or more of the anatomical features identified in the eye-tracking images after the reference time to determine a reaction time or other response of the first eye. In addition, the processor(s) may monitor changes in the orientation of the wearer's head after the reference time to determine a reaction time or other response of the wearer's head. Optionally, the processor(s) may analyze one or more of the determined reaction times to determine information regarding the wearer. For example, the reaction time of the wearer's head may be compared to the reaction time of the first eye to determine at least one of a physical or mental state of the wearer.

In an exemplary embodiment, the emitter may include one or more light sources mounted on the device for emitting light towards the first eye when activated. In another exemplary embodiment, the emitter may include one or more speakers mounted on the device for generating predetermined sounds.

Optionally, the one or more processors may include a controller coupled to the emitter for activating the emitter.

For example, the controller may be configured for intermittently activating the emitter, thereby providing a series of reference times. The processor(s) may compare the reaction time or other response of the wearer's head to the reaction time or other response of the first eye after each of the reference times, e.g., to determine at least one of a physical or mental state of the wearer. In one embodiment, the controller may periodically or randomly activate the emitter. In another embodiment, the system may include a receiver on the device coupled to the controller, and the controller may receive commands from a remote location, e.g., instructing the controller to activate the emitter based on the commands received by the receiver.

In accordance with yet another embodiment, a method is provided for determining reaction times or other responses that includes placing a device on a wearer's head, the device comprising a scene camera oriented away from the wearer and an eye-tracking camera oriented towards a first eye of the wearer; monitoring eye-tracking images from the eye-tracking camera to identify anatomical structures of the first eye; and monitoring scene camera images from the scene camera to identify predetermined events in the environment of the wearer. A reference time may be identified, e.g., when a predetermined event is identified from the scene camera images, and changes in one or more of the anatomical features identified in the eye-tracking images may be monitored to determine a reaction time or other response of the wearer to the predetermined event.

In accordance with still another embodiment, a method is provided for determining reaction times or other responses that includes placing a device on a wearer's head, the device comprising an eye-tracking camera oriented towards at least one of the wearer's eyes; monitoring eye-tracking images from the eye-tracking camera to identify anatomical structures of the first eye; and monitoring sounds within an environment of the wearer to identify predetermined events within the environment. A reference time may be identified, e.g., when a predetermined sound is detected within the environment, and changes in one or more of the anatomical features identified in the eye-tracking images may be monitored to determine a reaction time or other response of the wearer to the predetermined sound.

In accordance with another embodiment, a method is provided for determining reaction times or other responses that includes placing a device on a wearer's head, the device comprising an eye-tracking camera oriented towards at least one of the wearer's eyes; monitoring eye-tracking images from the eye-tracking camera to identify anatomical structures of the first eye; and monitoring an orientation of the wearer's head. At least one of the wearer and the wearer's environment may be monitored, e.g., to identify predetermined events, and a reference time may be identified when a predetermined event is detected. Changes in one or more of the anatomical features identified in the eye-tracking images after the reference time may be monitored to determine a reaction time or other response of the wearer to the predetermined event, and/or changes in the orientation of the wearer's head after the reference time may be monitored to determine a reaction time or other response of the wearer's head to the predetermined event. For example, the reaction times or other responses may be compared, e.g., to determine at least one of a physical or mental state of the wearer.

In accordance with yet another embodiment, a method is provided for determining reaction times or other responses that includes placing a device on a wearer's head, the device comprising an eye-tracking camera oriented towards at least one of the wearer's eyes, and monitoring eye-tracking images from the eye-tracking camera to identify anatomical structures of the first eye. A detectable signal, e.g., a sound or light, may be emitted towards the wearer at a reference time, and changes in one or more of the anatomical features identified in the eye-tracking images after the reference time may be monitored to determine a reaction time or other response of the wearer to the detectable signal. In addition or alternatively, changes in the orientation of the wearer's head after the reference time may be monitored to determine a reaction time or other response of the wearer's head to the detectable signal, e.g., to determine the wearer's physical and/or mental state.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIGS. 6A-6C show an example of a wearer's eye movement and pupillary reaction times resulting from the display of an image of a virtual object on a display monitor.

DETAILED DESCRIPTION OF THE EXEMPLARY EMBODIMENTS

Figure 1:
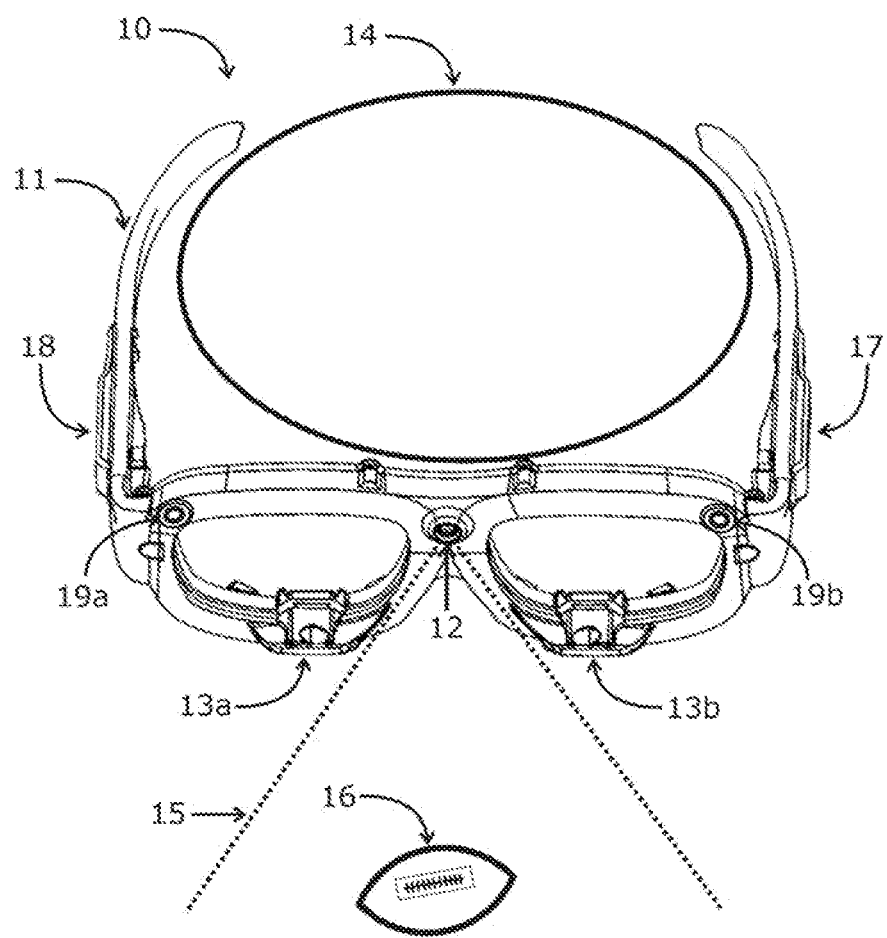
FIG. 1 is a perspective view of an example of a system mounted on eyeglasses frames for measuring reaction times of a wearer's head, eyes, eyelids, and/or pupils.

Turning to the drawings, FIG. 1 shows an exemplary embodiment of a system 10 including a set of eyeglass frames 11 with a scene camera 12, and two eye-tracking cameras 13*a*, 13*b*. The scene camera 12 is oriented on the frame 11 to view an area away from the wearer's head 14 in order to track the environment 15 in the region of the device wearer. For example, the scene camera 12 may be used to identify the movement of objects, such as a football 16, or any identifiable change in an object's or camera sub-region's size, brightness, geometry, color, and the like, e.g., in order to establish reference times for reaction time measurements, as described further below. The eye-tracking cameras 13*a* and 13*b* are oriented on the frame 11 toward the wearer's head 14 to track the locations of the wearer's eyelids, pupils, and/or other reference points in one or more eyes, such as the pupil, iris, or sclera (not shown).

In this embodiment, a single processing unit 17 may be carried by the frame 11 to acquire images from the scene camera 12 as well as the eye-tracking cameras 13a, 13b, although it will be appreciated that separate processors (not shown) may be provided on the frame 11 or at a remote location (not shown) that communicates with the frame 11. A self-contained power source (e.g., battery) 18 may be carried by the frame 11, e.g., encased in the stem of frame 11 opposite that containing processing unit 17.

In an exemplary embodiment, each of the scene camera 12 and eye-tracking cameras 13a, 13b may include a CCD or CMOS or other detector, e.g., including a rectangular or other active area array of pixels, for capturing images and generating video signals representing the images. The active area of the cameras 12, 13a, 13b may have any desired shape, e.g., a square or rectangular shape, and the like. In addition, the cameras 12, 13a, 13b may include one or more filters, lenses, and the like, if desired, e.g., to focus images on the active area, filter undesired intensities and/or wavelengths of light, and the like.

In the embodiment illustrated in FIG. 1, the scene camera 12 is unobtrusively located on the nose bridge of the frame 11, thereby minimizing interference with the wearer's normal vision. It is to be understood that multiple scene cameras may be included, pointed in any directions including the back, top, and sides of a wearer's head 14. For example, two (2) scene cameras 19a, 19b may be mounted at locations near the outer edges of the frame 11, e.g., in addition to or instead of the scene camera 12. In addition or alternatively, scene cameras may be located on the frame 11, e.g., to view an environment to the sides and/or to the rear of the device wearer (not shown). In the case of headwear, a scene camera may, for example, be located atop the wearer's head 14. Finally, fully or partially reflective surfaces that are stationary or moveable (not shown) may also be used to direct views in different directions to the active areas of one or more scene cameras.

It is to be understood that multiple scene cameras may be provided that are spaced apart from one another and/or directed toward multiple regions around the device wearer to provide separate or overlapping fields-of-view. Multiple scene cameras may provide higher spatial resolutions, increased sensitivity under different lighting conditions, and/or a wider field-of-view, e.g., in addition to or instead of scene camera 12. For example, multiple scene cameras may be used to detect objects (e.g., projectiles) approaching the device wearer from any direction. In addition or alternatively, another potential advantage of using multiple scene cameras is the ability to use different optical filters with each camera to isolate objects of interest that differ in color or that are preferentially illuminated using different wavelengths of electromagnetic radiation.

Figure 2:
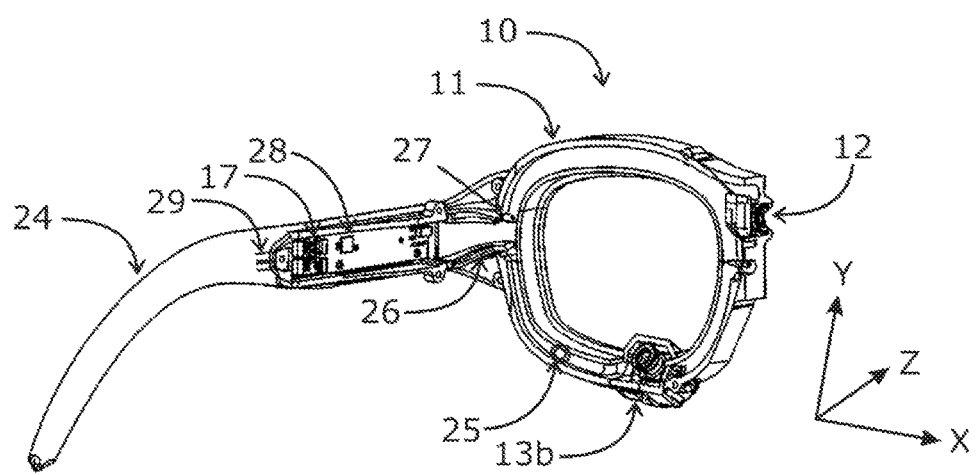
FIG. 2 is a partial cut-away, side view of the system of FIG. 1, showing connections among a processing unit, accelerometer, scene camera, eye-tracking camera, and other components.

FIG. 2 shows a cut-away view and back side of the system 10 illustrated in FIG. 1. The fixed spatial displacement between the scene camera 12 and eye-tracking camera 13b mounted within frame 11 in X, Y and Z directions may be readily seen from this perspective. This displacement may be used in calculations to determine eye gaze-tracking vectors similar to the embodiments described in the references incorporated by reference elsewhere herein. For example, gaze-tracking during reaction time measurements may be used to determine whether the device wearer looks toward or away from events in the environment 15 (FIG. 1) that trigger reactions. Looking toward versus looking away from an object or image may, for example, be used to assess whether the wearer is attracted by a scene or whether there is avoidance of particular types of visual images.

FIG. 2 also shows an example of a location where a processing unit 17 for scene analysis and eye-tracking may be embedded within the stem 24 of the frame 11. In this exemplary embodiment, a single processing unit 17 is in the form of a field-programmable gate array (FPGA), although alternatively, the processing unit 17 may be an application-specific integrated circuit (ASIC) or other processing device.

The processing unit 17 may include one or more controllers or processors, e.g., one or more hardware components and/or software modules for operating various components of the system 10. For example, the processing unit 17 may include a separate (not shown) or integral controller for controlling light sources or cameras 12, 13b, for receiving and/or processing signals from cameras 12, 13b, for receiving and/or processing signals from accelerometers 28, for wireless communication, and the like. Optionally, one or more components of the processing unit 17 may be carried on the stem 24, on the lens supports of the frame 11, nose bridge, and/or other locations within the eyewear or headwear, similar to the embodiments described in the references incorporated by reference elsewhere herein. In the exemplary embodiment shown in FIG. 2, a single processing unit 17 is used for image acquisition and processing for both scene identification and eye tracking functions, as well as other sensors and electronics, for reaction time measurements.

Cable(s) 26 may include individual cables or sets of wires coupled to the cameras 12, 13b, battery 18 (FIG. 1), light sources, and/or other components on the frame 11 and to the processing unit 17. For example, individual cables or sets of wires (not shown) may be embedded in the frame 11, e.g., along the rim from the cameras 12, 13b, and the like, until captured within the cable 26, e.g., to reduce the overall profile of the frame 11 and/or to direct signals around any hinged regions or corners 27 within the eyewear or headwear, as desired. Embedded cables and miniature electronics may reduce the obtrusiveness of the eyewear or headwear (e.g., reducing weight, size, and/or blockage of the potential visual field of the device wearer).

The processing unit 17 may also include memory (not shown) for storing image signals from the camera(s) 12, 13b, measurements of filters for editing and/or processing the image signals, and the like. Optionally, the frame 11 and/or processing unit 17 may include one or more transmitters and/or receivers (not shown) for transmitting data, receiving instructions, and the like. In addition or alternatively, at least some processing may be performed by components that are remote from the on-board processing unit 17 and frame 11, similar to embodiments disclosed in the references incorporated by reference elsewhere herein. For example, the system 10 may include one or more receivers, processors, and/or displays (not shown) at a remote location from the processing unit 17 and/or frame 11, e.g., in the same room, at a nearby monitoring station, or at a more distant location. Such displays may include views generated by the scene camera 12 or eye-tracking camera(s) 13b, and/or graphs or tables of measurements.

Accelerometer 28 may be provided on the frame 11, e.g., located near the processing unit 17 or elsewhere within the eyewear or headwear. A multi-axis accelerometer that detects accelerations in up to three (3) orthogonal directions may be used to detect movements of the wearer's head 14 (shown in FIG. 1) as well as overall wearer's head orientation relative to the gravitational field of the earth. The accelerometer 28 may be tuned to the g-forces normally encountered during movements of the wearer's head 14 (e.g., less than two (2) G's). It is to be understood that special purpose designs may be developed for specific situations. For example, higher sensitivity may be a requirement for infants or small animals; whereas a greater range might be required to monitor head movements of military fighter pilots where instantaneous forces might exceed nine (9) G's.

With additional reference to FIG. 2, a connector 29 may optionally be provided on the frame 11, e.g., to acquire electronic signals with reference time information from devices coupled to the system 10 by the connector 29. For example, a microphone (not shown) may be connected to the connector 29 to provide an input signal, and the reaction times or other responses (e.g., magnitude of response over time) of the wearer's eyes, eyelids, head, and/or pupils may be measured in response to the generation of a sound or a series of sounds. Alternatively, one or more microphones (not shown) may be mounted on the frame 11 that are coupled to the processing unit 17, e.g., for substantially continuously or intermittently monitoring the wearer's environment or the wearer for predetermined sounds. Reference times may, for example, be registered when the sound level reaches a threshold value. In other embodiments, waveform recognition techniques may be used to measure reaction times in response to specific words or phrases. For example, the microphone(s) may be used to listen to the wearer, and the processing unit 17 may detect when the wearer utters predetermined words or sounds, and then measure the reaction time or other response of the wearer after the reference time associated with the detected event. In addition or alternatively, the processing unit 17 may monitor the microphone signals to detect when a predetermined sound is generated within the wearer's environment, and the reaction time or other response of the wearer may determined from the reference time associated with the detected event.

Other substantially continuous or intermittent analog signals may be also used, for example, as generated by a position sensor, strain gauge, air flow sensor, thermometer, and the like, e.g., where a temporal reference is produced when the signal reaches a chosen threshold voltage or current. For example, a temporal reference may also be produced when a particular series of voltages or currents, or waveform is encountered. In addition or alternatively, digital signals with low-to-high and/or high-to-low transitions, i.e., binary transitions, may also be used as reference time inputs.

With additional reference to FIG. 2, optionally, one or more light-sources 25 may be included within the eyewear or headwear to produce a burst of light at one or more chosen times, for example, to evoke pupillary responses and/or measure reaction times and responses of the device wearer. In this exemplary embodiment, the reference time (i.e., activating the light source) may be controlled by a processing unit that controls the light source and the light source 25 may be a light-emitting diode (LED).

Multiple lights sources may also be included that may be positioned at various locations around the frame 11 of the eyewear or headwear. Multiple light sources with similar illumination characteristic may be used to provide a more wide-spread illumination of the wearer's eye to evoke responses. Multiple light sources may also be used to evoke responses in one eye individually or both eyes simultaneously. In addition or alternatively, multiple light sources with dissimilar properties may also be used, for example, to illuminate eyes with different wavelengths of light. Wavelengths of electromagnetic radiation may be in the visible spectrum or outside the visible spectrum.

The current or voltage used to control the one or more light sources 25 may also be varied in amplitude or duration to control the intensity of illumination. For example, varying the intensity of light sources may be used to determine threshold intensities that evoke pupillary responses (e.g., at selected wavelengths). In addition or alternatively, one or more speakers (not shown) may be provided, e.g., on the device or separate from the device, which may generate predetermined sounds together with or separate from activation of the light source(s) 25.

Figure 3:
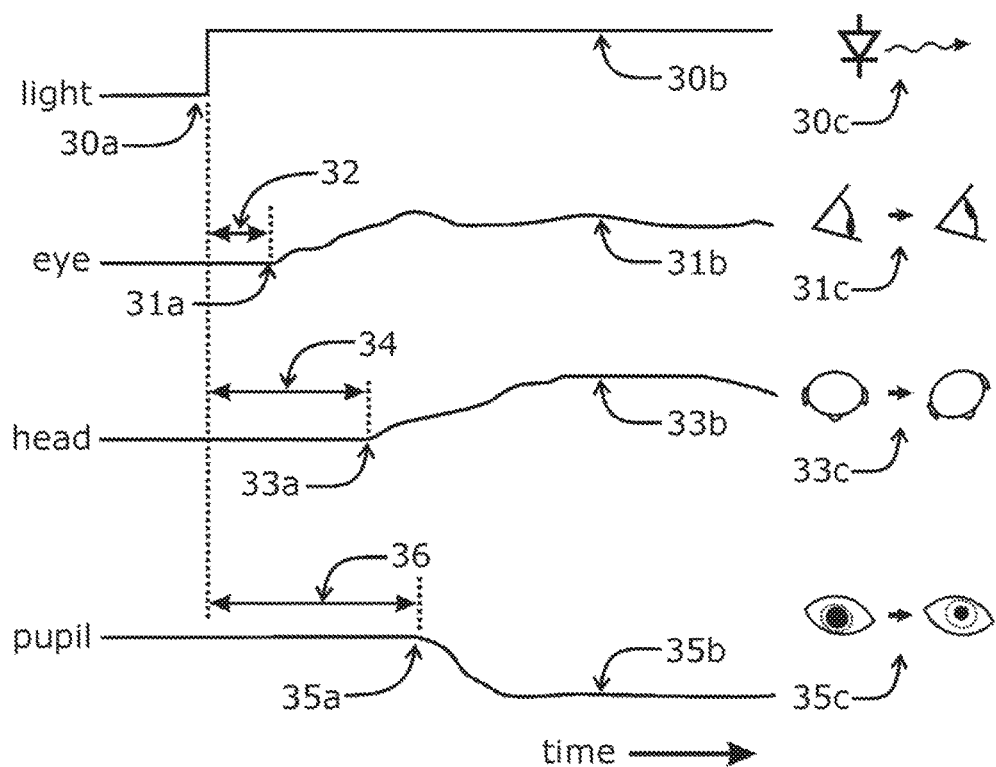
FIG. 3 is an example of measured responses and reaction times of a wearer's eye movement, head movement, and pupillary constriction in response to a flash of light.

Turning to FIG. 3, an exemplary sequence of events is shown, which may be used to measure reaction times of the wearer's eye movement, head movement, and/or pupil size in response to a flash of light. In this example, light is generated by a light emitting diode 30c at a chosen time 30a, thereby providing a reference time that may be compared to subsequently detected responses. For example, as shown in FIG. 2, one or more light sources 25 used to evoke responses may be mounted, if desired, on the eyewear or headwear such that light emitted by the light source(s) 25 are directed towards the wearer's eye(s). In addition or alternatively, light sources may also be provided separate from or external to the device wearer. Under these conditions, the time of occurrence of flashes of light and light intensity 30b may be measured by one or more scene cameras, if desired, e.g., to determine the reference time for detecting and/or monitoring one or more responses by the wearer.

FIG. 3 illustrates an example of device wearer eye movement 31c, e.g., where one or more eye-tracking cameras 13b (shown in FIG. 2) may be used to track one or more reference locations on the wearer's eye (e.g., edges of a pupil or iris, center of a pupil or iris, locations of regions of the sclera, and the like), e.g. to monitor eye movement 31c in one or two dimensions. Eye location trace 31b represents movement in one such dimension, e.g., along a vertical or "y" axis (shown in FIG. 2). As shown, signification eye movement begins to occur at a time 31a following the activation of the light source 30a. The temporal difference between activating the light source at time 30a and detecting significant movement of the wearer's eye at time 31a is the reaction time or response time 32 of the wearer's eye, i.e., the components of the eyeball, such as the pupil and iris, identified from the eye-tracking camera images. In addition, as shown, the magnitude of response of the wearer's eye, e.g., the location in one or more dimensions, may be measured over time, e.g., after time 31a when an initial reaction is detected.

FIG. 3 also illustrates an example of monitoring and/or identifying wearer head movement 33c, e.g., where a multiaxial accelerometer 28 (shown in FIG. 2) may be used to measure relative displacements of the head 14 (FIG. 1) in one or more dimensions. Head displacement trace 33b represents movement in one such dimension, e.g., within a horizontal plane and/or orthogonal to a vertical or "y" axis (shown in FIG. 2). As shown, signification head movement begins to occur at a time 33a following the activation of a light source at time 30a. The temporal difference between activating the light source 30a and detecting significant movement of the wearer's head at time 33a is the reaction time 34 of the wearer's head. Similar to the eye 31, in addition, if desired, the magnitude of response of the wearer's head, e.g., degree of turning, speed of turning, and the like, may be measured over time, e.g., after time 33a when an initial reaction is detected.

FIG. 3 also illustrates a pupillary response 35c to increased light levels, e.g., where one or more eye-tracking cameras 13b (shown in FIG. 2) may be used to track the size and/or geometry of one or both of the device wearer's pupils. Pupil size trace 35b represents changes in the area occupied by one pupil as measured by an eye-tracking camera 13b and associated processing unit 17 (shown in FIG. 2). In response to activating the light source 30a, the wearer's pupil begins to constrict at time 35a and continues to be constricted for as long as the light remains on. The temporal difference between activating the light source at time 30a and the onset of significant pupillary constriction at time 35a is the wearer's pupillary reaction time 36. In addition, the magnitude of response of the wearer's pupil, e.g., the size and/or shape of the pupil, may be measured over time, e.g., after time 35a when an initial reaction is detected.

Figure 4A:
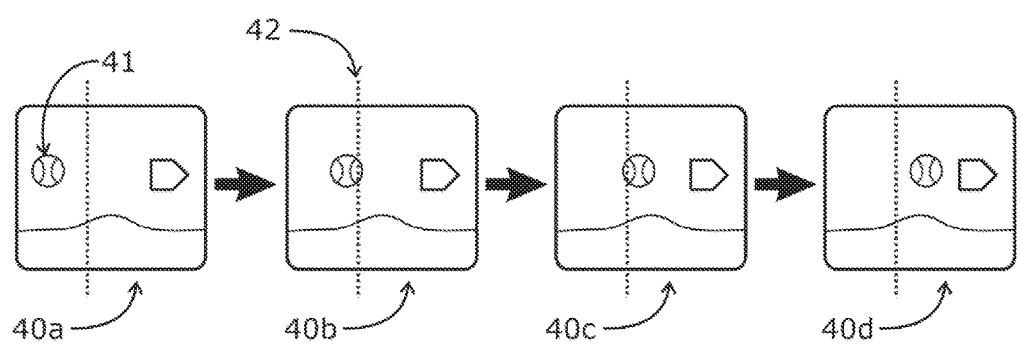
FIG. 4A is an example of camera images gathered by a scene camera tracking an object (i.e., a baseball)
Figure 4B:
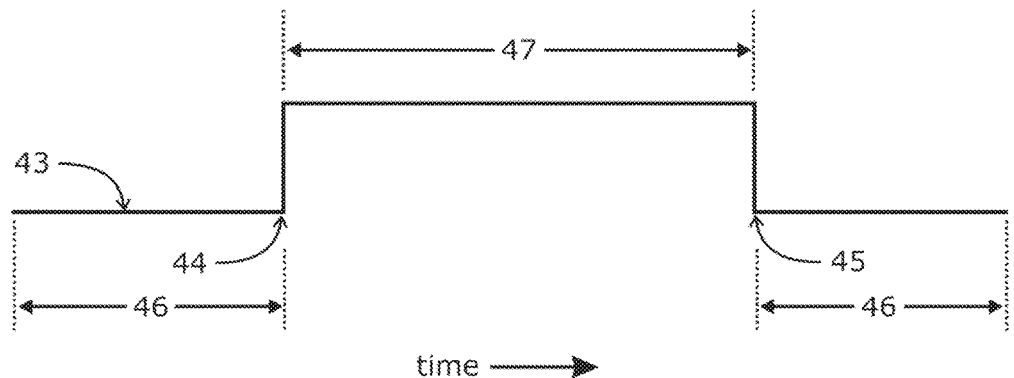
FIG. 4B is a graph showing an exemplary method to identify a reference time as the object passes through a selected scene reference location.

Turning to FIG. 4, exemplary methods are shown for using a scene camera 12 (e.g., as shown in FIG. 1) to generate one or more temporal reference points based on the movement of an object within a scene. A series of images 40a, 40b, 40c, 40d are shown that are selected from a video sequence gathered using a scene camera 12 (shown in FIG. 1). An object, represented in this case as a baseball 41, passes through the scene and may be identified and/or localized in images acquired by the scene camera 12, e.g., using machine vision techniques that are known in the art. For example, the processing unit 17 (e.g., shown in FIG. 1) may include or otherwise access a database of known templates, e.g., a table associating known objects with data identifying their shapes and/or colors. The database may include reference points of known objects, detailed color and/or shape information on the reference objects, and the like, mapped to particular physical objects, thereby providing the processing unit sufficient information to identify the encountered object, such as the baseball 41. When the object reaches a selected reference location or region 42 in the camera images 40a, 40b, 40c, 40d, a reference time is registered.

With additional reference to FIG. 4, it is possible to visualize the presence or absence of an object 41 at a selected location 42 in a camera image using a time trace 43. In this example, a low state 46 in the time trace represents the absence of an identifiable object at the selected location 42. Conversely, a high state 47 represents the presence of an identifiable object at the selected location or region 42. A low-to-high transition 44 provides a temporal reference point for the arrival of the object at the location. A high-to-low transition 45 may also be used as a temporal reference point, if desired, indicating the departure of the object. Similar strategies may be used to track multiple objects, traveling in multiple directions, traversing multiple reference locations or regions, and/or in multiple orientations within images generated by one or more scene cameras.

Figure 5:
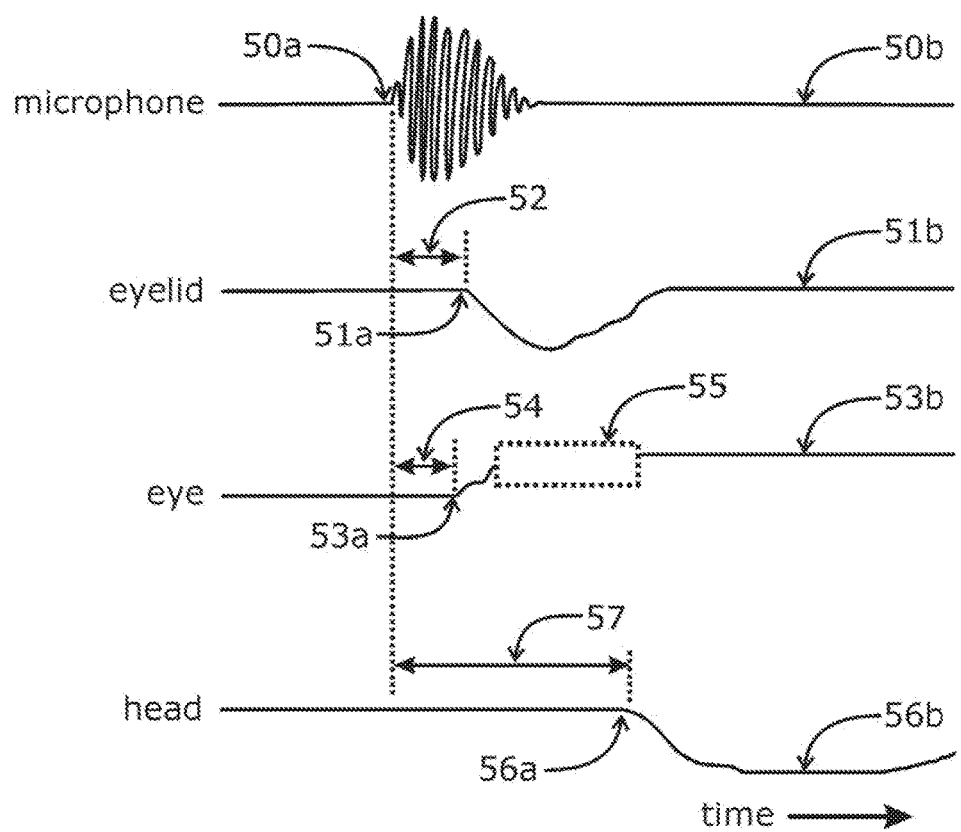
FIG. 5 is an example of measured reaction times of a wearer's eyelid, eye, and head in response to a sharp sound.

Turning to FIG. 5, additional exemplary methods are shown for measuring response times based on audible references, e.g., following the occurrence of a sharp sound. The system 10 may include a microphone (not shown), e.g., mounted on the frame 12 or elsewhere on eyewear or headwear, or positioned remotely with signals supplied to or oriented towards the eyewear or headwear and/or wearer, may be used to generate a sound represented by sound time trace 50b. The occurrence of a sound may be detected as the presence of vibrations (i.e., generated by traveling compression waves in the air and sensed by a microphone) on the trace 50b, e.g., where the onset of a sharp sound 50a may be used as a temporal reference point. Particular waveforms may also be identified to produce multiple distinct and/or periodic temporal reference points. For example, sounds associated with the formation of words may be identified using speech recognitions techniques that are known in the art, e.g., to identify particular words and trigger one or more temporal reference points.

One or more eye-tracking cameras 13b (FIG. 2) mounted on the eyewear or headwear may be used to track movement of one or both of the wearer's eyelids in order to generate an eyelid position trace 51b. In this case, closure of one eyelid is represented as a downward deflection in the eyelid position trace 51b starting at time 51a. In FIG. 5, the temporal difference between the occurrence of the sound, e.g., activation of the microphone at time 50a, and significant movement of the eyelid at time 51a is the reaction time 52 of the eyelid.

The same (or different) eye-tracking camera(s) mounted on the eyewear or headwear (e.g., cameras 13a, 13b shown in FIG. 1) may be used to track movement of reference locations of one or both wearer's eyes (e.g., edges of pupils, structures with the iris, and the like, similar to other embodiments herein), e.g., in order to generate one or multiple-dimensional eye location traces. With additional reference to FIG. 5, a representative trace is shown indicating the position in one dimension of one eye, e.g., along a vertical or "y" axis, as an eye location time trace 53b. The temporal difference between the occurrence of a sound 50a and significant movement of the eye at time 53a is the reaction time 54 of the eye. In this particular example, closure of the eyelid, as depicted in trace 51b, over the iris and pupil produces a brief time during which eye movement cannot be monitored, e.g., during time span 55, because of blockage of the view of the pupil and iris within eye-tracking camera images.

As described previously, a multi-dimensional accelerometer 28 (shown in FIG. 2) may be mounted on the eyewear or headwear and used to monitor movement of the head. As discussed earlier, accelerometers, for example based on MEMS technologies, may monitor accelerations in all three (3) orthogonal dimensions substantially simultaneously. With additional reference to FIG. 5, a representative trace indicating the movement of the head in a selected dimension is illustrated as a head location time trace 56b. The temporal difference between the occurrence of the sound at time 50a and significant movement of the head at time 56a is the reaction or response time 57 of the head.

Turning to FIGS. 6A-6C, another exemplary method is shown for measuring the reaction times (and/or optionally other responses) of structures of the eye in response to the display of one or more virtual objects, e.g., presented via a picture, book, computer monitor, mobile computing device, television, theater screen, billboard, and the like. In this example, as shown in FIGS. 6A and 6B, a system may be provided that includes a eyewear or headwear device for monitoring a user or wearer (not shown, e.g., the system 10 shown in FIG. 1) and a system including a computer display monitor 60a, 60b for displaying images to the wearer. As shown in FIG. 6B, the monitor 60b may be used to depict the occurrence of an explosion or other sudden image 61, e.g., replacing other previous images (not shown) presented on the monitor 60a, as shown in FIG. 6A. The time that the initial image of the explosion 61 is displayed on the monitor 60b may be recorded or otherwise known by the system as a reference time, e.g., provided by a computer, processor, or other electronic device coupled to the monitor 60 for generating the image(s). The reference time may be transmitted to a processor, e.g., in frame 12 of the system 10 (shown in FIG. 1) or elsewhere, or image recognition from scene images using one or more scene cameras 12 (e.g., shown in FIG. 1) may be used to measure the time of first appearance of the sudden image 61 to register a reference time. The explosion display reference time is depicted as a low-to-high transition 66a on image display time trace 66b of FIG. 6C.

FIGS. 6A-6C further illustrate a reaction by a wearer's eye 62 to the display of the virtual explosion 61. For example, prior to the display of the virtual explosion 61, an eye-tracking camera 13a, 13b (e.g., shown in FIG. 1) may acquire images that show the eye 62a with a pupil 63a of typical size, e.g., for room-lit or other ambient conditions. The pupil 63a is surrounded by an iris 64 which, in turn, is surrounded by the "white of the eye" or sclera 65. Following the display of the explosion 61, measurements of the eye 62b from images acquired by the eye-tracking camera may reveal that the center of the pupil 63b has moved and/or that the pupil 63b has significantly dilated. Eye movement in a selected dimension, e.g., along a vertical or "y" axis, is depicted in an eye location time trace 67b in FIG. 6C, where the time of occurrence of initial eye movement in response to the virtual explosion is registered at time 67a. The temporal difference between the display of an explosion 61 at time 66a and significant movement of the eye at time 67a is the reaction or response time 67c of the eye.

In addition or alternatively, the size of the pupil 63 may be tracked using an eye-tracking camera 13a, 13b (e.g., shown in FIG. 1) and depicted as a time trace 68b in FIG. 6C, where the time of onset of pupil dilation in response to a virtual explosion 61 is marked 68a. The temporal difference between the display of an explosion 61 at time 66a and significant pupil dilation at time 68a is the pupillary reaction or response time 68c. Tracking the combination of whether a response to the display of an image causes attraction (i.e., focus) or aversion to the image along with measuring the degree of pupillary dilation may, for example, assist in the diagnosis of post traumatic stress disorder and/or to measure the effectiveness of advertising. Thus, the integration of reaction times and/or magnitudes of multiple responses by a wearer may be monitored to more accurately diagnose, predict, and/or analyze behavior of the wearer than monitoring eye movement or another parameter alone.

Figure 7A:
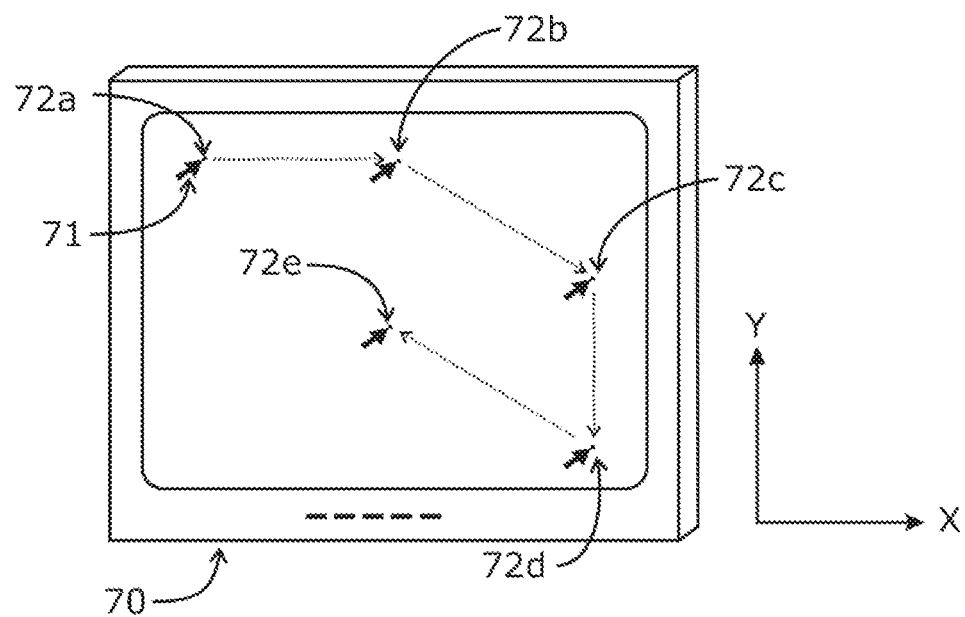
FIGS. 7A and 7B show an example of repeatedly measuring a wearer's eye movement reaction times in response to following a virtual object (i.e., a cursor) as it moves about on a display monitor.
Figure 7B:
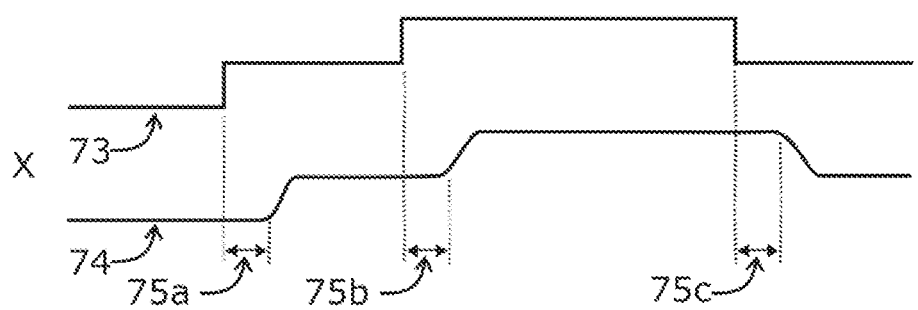
Figure 7B:
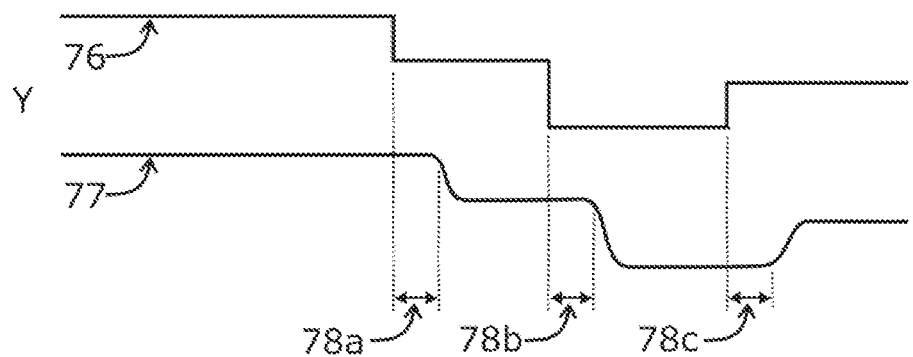

FIGS. 7A and 7B illustrate the ability of the systems and methods described herein to make repeated reaction time measurements. In this example, the device wearer of a system, such as the system 10 of FIG. 1, may be asked to visually track a virtual object, e.g., a computer cursor 71, around the screen of a display monitor 70, as shown in FIG. 7A. The device wearer may be instructed to follow the cursor 71 as it is stepped through a series of screen locations 72a, 72b, 72c, 72d, 72e over a period of time. The times when cursor locations 72a, 72b, 72c, 72d, 72e are changed are known to the computer generating the display and may be transmitted to the system 10, or image recognition using one or more scene cameras 12 (e.g., as shown in FIG. 1) may be used to measure shifts in cursor location to generate a series of reference times.

With additional reference to FIG. 7A, where images are displayed on a two-dimensional screen 70, cursor locations 72a, 72b, 72c, 72d, 72e may be described by a pair of orthogonal coordinates, e.g., representing "X" (e.g., horizontal) and "Y" (e.g., vertical) dimensions within the plane of the screen 70. Movements in the X direction may be used to generate a time trace 73 for X-axis displacements, as shown in FIG. 7B. Eye movements may be tracked using an eye-tracking camera 13a, 13b (e.g., as shown in FIG. 1). Displacements by an eye in the X direction may be used to generate an eye location time trace 74, also as shown in FIG. 7B. Differences between the times of occurrence of cursor movements in the X direction and corresponding initial movements of the eye in the X direction may be used to generate a series of X-direction reaction times 75a, 75b, 75c.

Similarly, movements in the Y direction may be used to generate an eye location time trace 76 for Y-axis displacements. Displacements by an eye measured in the Y direction may be used to generate an additional eye location time trace 77, as shown in FIG. 7B. Differences between the times of occurrence of cursor movements in the Y direction and corresponding initial movements of the eye in the Y direction may be used to generate a series of Y-direction reaction times 78a, 78b, 78c of the device wearer. Differences in reaction times in horizontal and vertical directions may indicate the presence of a muscular or neurological disorder. Changes in X- and Y-direction reaction times over a prolonged period may, for example, be used to assess fatigue.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented methods and/or processes as a particular sequence of steps. However, to the extent that the methods or processes do not rely on the particular order of steps set forth herein, the methods or processes should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A system for determining responses of a subject, comprising:
   a device configured to be worn on a wearer's head;
   an eye-tracking camera mounted on the device oriented towards a first eye of the wearer for capturing eye-tracking images of the first eye;
   a scene camera mounted on the device oriented away from the wearer for viewing an environment of the wearer and capturing scene camera images of the environment; and
   one or more processors coupled to the eye-tracking camera for identifying anatomical structures of the first eye within the eye-tracking images, the one or more processors configured for identifying reference times of external events based on object recognition algorithms used to identify objects and locations of objects within a field-of-view of the scene camera from the scene camera images, the one or more processors identifying reference times based on the times when predetermined objects are present at or absent from predetermined locations in the scene camera images and analyzing the eye-tracking images after the reference times to determine at least one of magnitudes of responses and reaction times of the first eye, eyelid, and pupil to the external events.

2. The system of claim 1, wherein the one or more processors are configured to identify, based on the eye-tracking images, two or more parameters selected from: a)

location of at least one of the pupil and iris in one or more dimensions, b) a size of the pupil, c) a shape of the pupil, and d) a location of the eyelid from the eye-tracking images, the one or more processors detecting changes in the two or more parameters to determine at least one of magnitudes of responses and reaction times of the wearer.

3. The system of claim 1, wherein the object recognition algorithms identify the objects based at least in part on a shape of the object.

4. The system of claim 1, wherein the object recognition algorithms identify the objects based at least in part on a color of the object.

5. The system of claim 1, wherein the object recognition algorithms identify the objects based at least in part on a brightness of the object.

6. The system of claim 1, wherein the one or more processors are configured for generating a binary signal identifying the presence versus absence of an object at a selected location in the scene camera images to generate a reference time.

7. The system of claim 1, wherein the one or more processors are configured to analyze the scene camera images for scene movements to determine movements of the wearer's head.

8. The system of claim 7, wherein the one or more processors are configured to determine at least one of magnitudes of responses and reaction times of the wearer's head based on reference times and head movements of the wearer.

9. The system of claim 1, further comprising a microphone for detecting sounds within the wearer's environment, the one or more processors coupled to the microphone for identifying predetermined sounds from the wearer's environment as a reference time.

10. The system of claim 1, further comprising a sound generator for generating a digital signal, the one or more processors coupled to the sound generator for identifying activation of the sound generator as a reference time.

11. The system of claim 1, further comprising an environmental sensor for generating an analog signal, the one or more processors coupled to the environmental sensor for identifying activation of the environment sensor as a reference time.

12. The system of claim 1, claim 1, wherein the eye tracking camera comprises one of a charge-coupled device (CCD) and complementary metal-oxide semiconductor (CMOS) detector.

13. The system of claim 1, claim 1, wherein the one or more processors each comprises one of a field-programmable gate array (FPGA) and application-specific integrated circuit (ASIC).

14. The system of claim 1, further comprising at least one additional scene camera for capturing images of the environment of the wearer.

15. The system of claim 1, further comprising a second eye-tracking camera mounted on the device oriented towards a second eye of the wearer for capturing eye-tracking images of the second eye, the one or more processors analyzing the eye-tracking images after the reference times to determine at least one of magnitudes of responses and reaction times of the second eye, eyelid, and pupil to the external events.

16. The system of claim 1, further comprising a light source mounted on the device for emitting light towards the first eye, the one or more processors coupled to the light source for identifying activation of the light source as a reference time.

17. The system of claim 16, claim 1, wherein the light source comprises one or more light-emitting diodes (LEDs).

18. A system for determining magnitudes of responses, comprising:
a device configured to be worn on a wearer's head;
a scene camera mounted on the device oriented away from the wearer for viewing an environment of the wearer and capturing scene camera images of the environment;
an eye-tracking camera mounted on the device oriented towards a first eye of the wearer for capturing eye-tracking images of the first eye; and
one or more processors coupled to the eye-tracking camera for identifying anatomical structures of the first eye within the eye-tracking images, the one or more processors configured for identifying reference times of external events based on a change in a characteristic or location of an object identified from the scene camera images, wherein the characteristic comprises one or more of a brightness level, color, size, or shape of the object, and analyzing the eye-tracking images after the reference times to determine magnitudes of responses of the first eye, eyelid, and pupil to the external events.

* * * * *

UNITED STATES PATENT AND TRADEMARK OFFICE
CERTIFICATE OF CORRECTION

PATENT NO. : 9,931,069 B2
APPLICATION NO. : 14/569303
DATED : April 3, 2018
INVENTOR(S) : Nelson G. Publicover et al.

It is certified that error appears in the above-identified patent and that said Letters Patent is hereby corrected as shown below:

In the Claims

At Column 21, Line 43, please correct "system of claim 1, claim 1, wherein" to be --system of claim 1, wherein--

At Column 22, Line 1, please correct "system of claim 1, claim 1, wherein" to be --system of claim 1, wherein--

At Column 22, Line 22, please correct "system of claim 16, claim 1, wherein" to be --system of claim 16, wherein--

Signed and Sealed this
Second Day of July, 2019

Andrei Iancu
*Director of the United States Patent and Trademark Office*